United States Patent
Wada et al.

(10) Patent No.: US 10,271,874 B2
(45) Date of Patent: Apr. 30, 2019

(54) SURGICAL TOOL INSERTION AID

(71) Applicants: KEIO UNIVERSITY, Tokyo (JP);
KABUSHIKI KAISHA TOP, Tokyo (JP)

(72) Inventors: Norihito Wada, Tokyo (JP); Takuya Miyazaki, Tokyo (JP); Yoshihiko Himura, Tokyo (JP)

(73) Assignees: KEIO UNIVERSITY, Tokyo (JP);
KABUSHIKI KAISHA TOP, Tokyo (JP)

(*) Notice: Subject to any disclaimer, the term of this patent is extended or adjusted under 35 U.S.C. 154(b) by 144 days.

(21) Appl. No.: 15/111,663

(22) PCT Filed: Jan. 9, 2015

(86) PCT No.: PCT/JP2015/050500
§ 371 (c)(1),
(2) Date: Jul. 14, 2016

(87) PCT Pub. No.: WO2015/107994
PCT Pub. Date: Jul. 23, 2015

(65) Prior Publication Data
US 2016/0331402 A1    Nov. 17, 2016

(30) Foreign Application Priority Data
Jan. 15, 2014  (JP) .................. 2014-005415

(51) Int. Cl.
| A61B 1/00 | (2006.01) |
| A61B 17/34 | (2006.01) |
| A61B 1/005 | (2006.01) |
| A61B 1/012 | (2006.01) |
| G02B 23/24 | (2006.01) |
| A61B 17/00 | (2006.01) |

(52) U.S. Cl.
CPC ........ *A61B 17/3423* (2013.01); *A61B 1/0014* (2013.01); *A61B 1/0055* (2013.01);
(Continued)

(58) Field of Classification Search
CPC ........ A61B 17/3423; A61B 2017/3425; A61B 2017/3427; A61B 2017/3447; A61B 2017/3445
See application file for complete search history.

(56) References Cited

U.S. PATENT DOCUMENTS

| 2004/0138529 A1* | 7/2004 | Wiltshire ............. A61B 1/0055 600/144 |
| 2005/0085691 A1 | 4/2005 | Nakao |

(Continued)

FOREIGN PATENT DOCUMENTS

| JP | 62-167531 | 7/1987 |
| JP | H10-192226 | 7/1998 |

(Continued)

OTHER PUBLICATIONS

Singaporean Office Action (Search Report/Written Opinion) dated Aug. 28, 2017, 9 pages.

(Continued)

*Primary Examiner* — Julianna N Harvey
(74) *Attorney, Agent, or Firm* — Rankin, Hill & Clark LLP

(57) ABSTRACT

A surgical tool insertion aid is provided which enables simultaneous use of multiple surgical tools, as well as the independent exchange of a surgical tool during surgery. A tubular surgical tool insertion aid 1 aids insertion of surgical tools 11 and 13 into the body, and includes: an inner tube 2 into which the surgical tools 11 and 13 are insertable, and which is insertable into the surgical tool insertion aid 1; and a plurality of guide members 3 which are extended in the axial direction from a distal end side to a proximal end side in the inner peripheral surface of the surgical tool insertion aid 1. The inner tube 2 includes, on the outer peripheral
(Continued)

surface thereof, an engaging member 4 that engages with the guide member 3 to be made slidable.

17 Claims, 10 Drawing Sheets

(52) U.S. Cl.
CPC ...... *A61B 1/00105* (2013.01); *A61B 1/00154* (2013.01); *A61B 1/012* (2013.01); *A61B 17/3494* (2013.01); *A61B 17/3498* (2013.01); *G02B 23/2476* (2013.01); *A61B 2017/00942* (2013.01); *A61B 2017/345* (2013.01); *A61B 2017/3419* (2013.01); *A61B 2017/3445* (2013.01); *A61B 2017/3447* (2013.01); *A61B 2017/3466* (2013.01)

(56) References Cited

U.S. PATENT DOCUMENTS

| | | | | |
|---|---|---|---|---|
| 2008/0249504 | A1* | 10/2008 | Lattouf | A61B 17/3421 604/511 |
| 2008/0262431 | A1 | 10/2008 | Anderson et al. | |
| 2009/0326462 | A1 | 12/2009 | Wingardner, III et al. | |
| 2010/0048992 | A1 | 2/2010 | Okada et al. | |
| 2011/0166422 | A1* | 7/2011 | Ross | A61B 1/00154 600/204 |
| 2012/0209267 | A1* | 8/2012 | Lee | A61B 17/7283 606/62 |

FOREIGN PATENT DOCUMENTS

| | | |
|---|---|---|
| JP | 2007-511247 | 5/2007 |
| JP | 2011-515127 | 5/2011 |
| JP | 2011-245017 | 12/2011 |
| WO | 2004/103430 | 12/2004 |
| WO | 2007/063904 | 6/2007 |
| WO | 2009/114837 | 9/2009 |
| WO | 2011/056848 | 5/2011 |

OTHER PUBLICATIONS

International Search Report, dated Apr. 21, 2015 (Apr. 21, 2015).
European Search Report dated Sep. 15, 2017, 7 pages.

* cited by examiner

SURGICAL TOOL INSERTION AID

TECHNICAL FIELD

The present invention relates to a tubular surgical tool insertion aid which aids insertion of a surgical tool such as an endoscope or forceps into the body when inserting the surgical tool.

BACKGROUND ART

In the field of medical treatment, when inserting a surgical tool into the body, a tubular surgical tool insertion aid is used which aids insertion of the surgical tool.

Conventionally, as a surgical tool insertion aid, a multi-lumen tube endoscope is known in which a plurality of flexible tubes are integrally fixed as inner tubes that form an image guide conduit, a light guide conduit, a treatment channel conduit, an air/water feeding channel conduit or the like.

According to the aforementioned surgical tool insertion aid, because the diameter and shape of a conduit can be ensured by means of a flexible tube, the insertability of a surgical tool can be improved at a time of use (for example, see Patent Literature 1).

CITATION LIST

Patent Literature

Patent Literature 1: Japanese Patent Laid-Open No. 62-167531

SUMMARY OF INVENTION

Technical Problem

However, when using a surgical tool insertion aid there is the disadvantage that it is not possible to insert a surgical tool having a larger diameter than the diameter of an inner tube, and furthermore, it is not possible to simultaneously use a number of surgical tools that exceeds the number of inner tubes.

An object of the present invention is to overcome the aforementioned disadvantage and provide a surgical tool insertion aid in which the diameters and number of inner tubes can be changed.

Solution to Problem

To achieve the aforementioned object, the present invention provides a surgical tool insertion aid having a tubular shape which aids insertion of a surgical tool into a body, including: a plurality of inner tubes into which the surgical tool is insertable and which are insertable into the surgical tool insertion aid, and which include at least one inner tube and another inner tube having a smaller diameter than the at least one inner tube; and a plurality of guide members which are extended in an axial direction from a distal end side to a proximal end side in an inner peripheral surface of the surgical tool insertion aid, and in which cross-sections perpendicular to an axial direction are of identical shapes; wherein each of the inner tubes includes, on an outer peripheral surface, an engaging member which engages with the plurality of guide members, respectively, to be made slidable.

Since the guide member is extended in the axial direction from the distal end side to the proximal end side in the inner peripheral surface of the surgical tool insertion aid of the present invention, by engaging the engaging member with the guide member and sliding the engaging member, the inner tube can be inserted into the surgical tool insertion aid without rotating the inner tube. Since a plurality of the guide members are provided in the surgical tool insertion aid, the inner tube can be inserted into the surgical tool insertion aid in a state in which the position thereof relative to another of the inner tubes is maintained. By inserting the surgical tools into each of the plurality of inner tubes, a plurality of surgical tools can be used simultaneously.

Further, in the surgical tool insertion aid of the present invention, since each of the inner tubes is independently slidable along the guide member through the engaging member, one inner tube can be withdrawn from the surgical tool insertion aid and another inner tube can be inserted into the space in which the one inner tube had been inserted in the surgical tool insertion aid. Further, a plurality of other inner tubes having a smaller diameter than the one inner tube can be inserted into the space in which the one inner tube had been inserted in the surgical tool insertion aid.

Therefore, according to the surgical tool insertion aid of the present invention, the diameter and number of inner tubes can be freely changed. By this means, the surgical tools can be independently exchanged during surgery, and desired surgical tools can be used.

In the surgical tool insertion aid of the present invention, the engaging member may be provided from a distal end to a proximal end of the outer peripheral surface of the inner tube, or the engaging members are provided at part of an area from the distal end to the proximal end of the outer peripheral surface of the inner tube, with at least one engaging member being provided at the distal end.

In the former case, the inner tube can be inserted more smoothly into the surgical tool insertion aid, and can be reliably prevented from interfering with another of the inner tubes that is already mounted inside the surgical tool insertion aid. Further, in the latter case, even in a case where the surgical tool insertion aid is bent, the inner tube can be inserted more smoothly into the surgical tool insertion aid.

In the surgical tool insertion aid of the present invention, preferably the outer peripheral surface of the inner tube is subjected to a hydrophilic treatment. In such a case, insertion of the inner tube can be performed with greater ease.

In the surgical tool insertion aid of the present invention, the inner tube may comprise a first inner tube having a first inner diameter, and a second inner tube having a second inner diameter. By using an inner tube having an inner diameter which is compatible with the outer diameter of the surgical tool, various surgical tools can be used in the surgical tool insertion aid.

Further, the surgical tool insertion aid of the present invention preferably comprises a first wire member which is embedded within a peripheral wall of the surgical tool insertion aid in an axial direction from the distal end side to the proximal end side thereof, and whose proximal end portion can be gasped and operated so as to cause the surgical tool insertion aid to bend in an arbitrary direction. By grasping and operating the proximal end portion of the first wire member, the surgical tool insertion aid can be caused to bend in an arbitrary direction and the distal end of the surgical tool insertion aid can be pointed at a desired position.

Furthermore, in a case where the surgical tool insertion aid includes the first wire member, preferably the surgical tool insertion aid includes a first wire fixing device which temporarily fixes an operation of the first wire member. The shape of the first wire member can be temporarily fixed by the first wire fixing device to maintain a state in which the distal end portion of the surgical tool insertion aid points in a predetermined direction.

In addition, the surgical tool insertion aid of the present invention preferably includes a second wire member which is fixed in the inner tube and whose proximal end portion can be grasped and operated so as to cause the inner tube to bend in an arbitrary direction. By grasping and operating the proximal end portion of the second wire member, the distal end of the inner tube can be caused to bend in an arbitrary direction, and the distal end of the inner tube can be pointed at a desired position. In addition, when the distal end of the inner tube is housed inside the surgical tool insertion aid, the surgical tool insertion aid can be caused to bend so as to follow the bending of the inner tube.

Further, in a case where the surgical tool insertion aid includes the second wire member, preferably the surgical tool insertion aid includes a second wire fixing device that temporarily fixes an operation of the second wire member. The shape of the second wire member can be temporarily fixed by the second wire fixing device to maintain a state in which the distal end portion of the inner tube points in a predetermined direction.

Furthermore, in a case where the surgical tool insertion aid includes the second wire member, preferably the inner tube comprises, on a distal end side, a bending portion that can be bent by an operation of the second wire member. By bending the inner tube at the bending portion, treatment with the surgical tool can be performed with greater ease.

In addition, preferably, in the inner tube, bending directions of the bending portion are limited. According to the aforementioned configuration, the inner tube can be bent only in directions which the surgeon intends, and operation of the inner tube can be performed with greater ease.

Further, preferably the surgical tool insertion aid of the present invention includes a first degassing prevention cap which is mounted at a proximal end portion of the surgical tool insertion aid and which is capable of introducing the inner tube. By means of the first degassing prevention cap, it is possible to prevent the leakage of air inside a body cavity from a place at which the inner tube is not inserted in the surgical tool insertion aid or from an outer peripheral portion of the inner tube that is inserted.

Preferably, the first degassing prevention cap includes a flexible sheet member which blocks the proximal end portion of the surgical tool insertion aid, and the sheet member includes a slit portion which penetrates in a thickness direction and which is provided for introducing the inner tube. When the inner tube is inserted in the surgical tool insertion aid, the inside of the body cavity can be kept airtight by the slit portion closely contacting the outer peripheral surface of the inner tube and the engaging member.

Further, when the surgical tool insertion aid includes the first degassing prevention cap, preferably the engaging member is provided from a distal end to a proximal end of the outer peripheral surface of the inner tube, and the inner tube includes, within a first predetermined distance from the proximal end thereof, a level-difference eliminating portion which fills a level difference between the outer peripheral surface of the inner tube and an outer peripheral surface of the engaging member.

Since a level difference that is formed as a result of the engaging member protruding from the outer peripheral surface of the inner tube is eliminated by the level-difference eliminating portion, the inside of the body cavity can be maintained in a more airtight state.

The surgical tool insertion aid of the present invention preferably includes a second degassing prevention cap which is mounted at a proximal end portion of the inner tube and which is capable of introducing the surgical tool. By means of the second degassing prevention cap, leakage of air within the body cavity from the inner tube in which the surgical tool is not inserted can be prevented. For example, an opening and closing valve can be used as the second degassing prevention cap.

In this connection, although the surgical tool insertion aid of the present invention can also be used in a manner in which a route of entry is opened in the skin and mucous membrane on the body surface and the surgical tool insertion aid is then inserted into the body from the opening, it is also possible to use the surgical tool insertion aid of the present invention in natural orifice translumenal endoscopic surgery (NOTES) in which the surgical tool insertion aid is inserted from a natural orifice such as the oral cavity, a route of entry is opened in a luminal wall of a gastrointestinal tract or the like, such as in the stomach or intestines, and a surgical tool is inserted into the body cavity from the opening via the luminal wall to perform treatment.

Therefore, the surgical tool insertion aid of the present invention preferably includes, on an outer peripheral side of the surgical tool insertion aid, an outer tube which is mounted in an advanceable and retractable manner with respect to the surgical tool insertion aid, or is rotatably mounted with respect to the surgical tool insertion aid as an axis.

Since the outer tube is mounted in an advanceable and retractable manner with respect to the surgical tool insertion aid, it is possible to advance only the surgical tool insertion aid in a state in which the position of the outer tube is fixed, and thereby bring the distal end of the surgical tool insertion aid closer to a desired position. Further, the inner tube that is disposed inside the distal end portion of the surgical tool insertion aid can be set to a desired position by rotating the surgical tool insertion aid relative to the outer tube in a state in which the position of the outer tube is fixed.

Further, when the surgical tool insertion aid includes the outer tube, preferably the surgical tool insertion aid includes two balloon members which are provided on the outer peripheral surface of the outer tube and which are contractible and expandable so as to protrude in an outer periphery direction, wherein a predetermined gap is provided between the two balloon members.

By including the two balloon members on the outer peripheral surface of the outer tube, after the surgical tool insertion aid is inserted into a body cavity from an opening formed in a luminal wall, and the luminal wall is positioned in the gap, the two balloons can be expanded to sandwich and fix the luminal wall between the two balloon members, and thus air and body fluid or the like can be prevented from leaking out from between the surgical tool insertion aid and the opening.

BRIEF DESCRIPTION OF DRAWINGS

FIGS. 2A, 2B, and 2C are multiple-view explanatory drawings illustrating cross-sections of a guide member, in which FIG. 2A illustrates a guide member having an approximately trapezoidal cross-section. FIG. 2B illustrates a guide member having an approximately circular cross-section, and FIG. 2C illustrates a guide member having a rectangular cross-section.

FIGS. 3A, 3B, and 3C are multiple-view explanatory drawings illustrating an inner tube, in which FIG. 3A illustrates an inner tube on which a long engaging member is provided, FIG. 3B illustrates a cross-section of the engaging member shown in FIG. 3A, and FIG. 3C illustrates an inner tube on which short engaging members are provided.

FIGS. 4A, 4B, and 4C are multiple-view explanatory drawings illustrating a bending portion of an inner tube, in which FIG. 4A illustrates a bending portion according to a pattern 1, FIG. 4B is a cross-sectional view along a line B-B in FIG. 4A, and FIG. 4C illustrates a bending portion according to a pattern 2.

FIGS. 5A and 5B are multiple-view explanatory drawings illustrating a bending portion of an inner tube, in which FIG. 5A illustrates a bending portion according to a pattern 3, and FIG. 5B is a cross-sectional view along a line B-B in FIG. 5A.

FIGS. 8A and 8B are multiple-view explanatory drawings illustrating a degassing prevention cap for a surgical tool insertion aid, in which FIG. 8A is a cross-sectional view, and FIG. 8B is a plan view.

FIGS. 9A and 9B are multiple-view explanatory drawings illustrating an inner tube comprising a level-difference eliminating portion, in which FIG. 9A is a perspective view, and FIG. 9B is a cross-sectional view along a line B-B in FIG. 9A.

FIGS. 10A and 10B are multiple-view explanatory drawings illustrating a usage state of the degassing prevention cap for a surgical tool insertion aid, in which FIG. 10A illustrates a usage state on an inner tube to which a level-difference eliminating tube is not mounted, and FIG. 10B illustrates a usage state on an inner tube to which a level-difference eliminating tube is mounted.

DESCRIPTION OF EMBODIMENT

Next, an embodiment of the present invention will be described in detail referring to the accompanying drawings.

Figure 1:
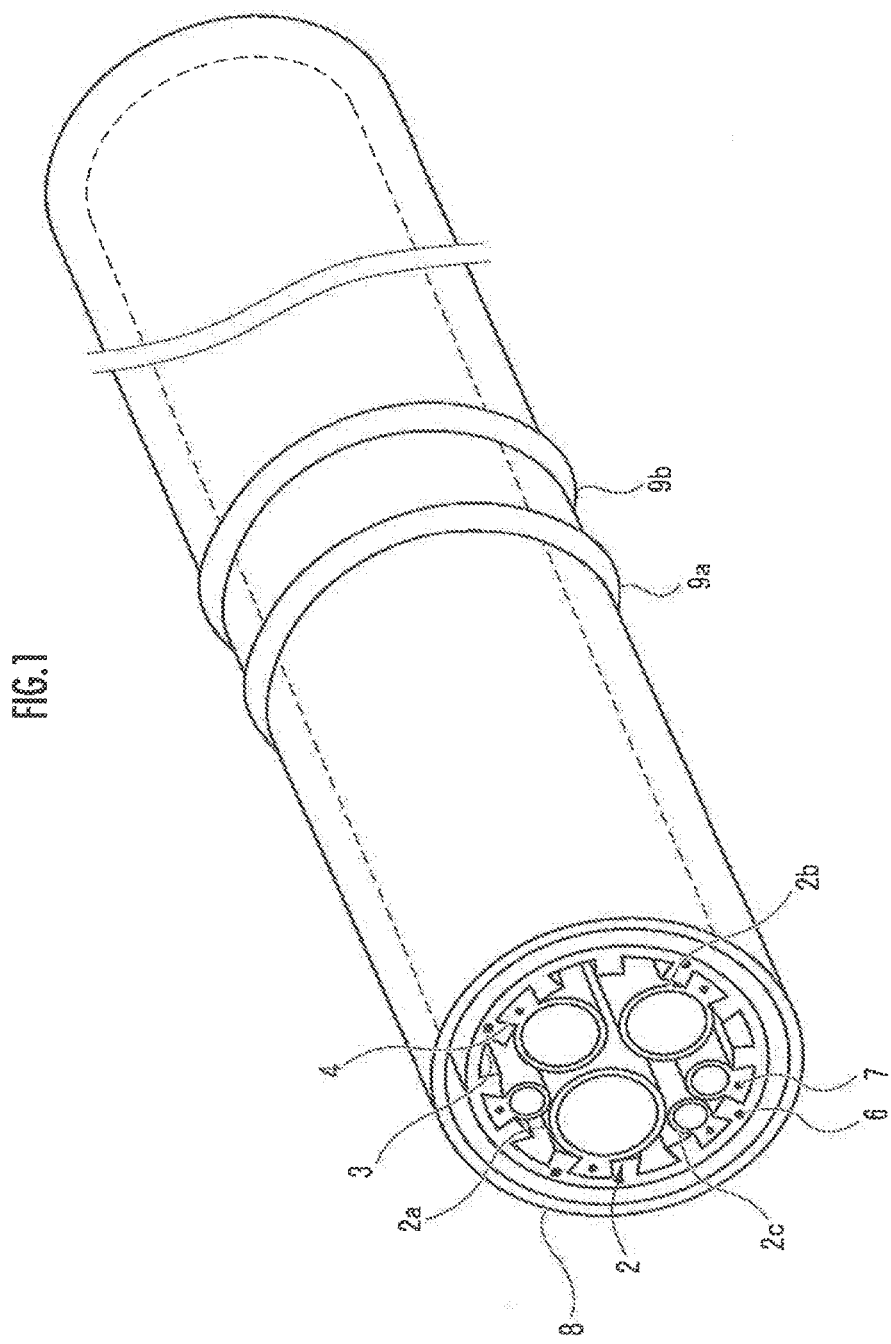
FIG. 1 is an explanatory drawing illustrating a surgical tool insertion aid according to an embodiment of the present invention.

A surgical tool insertion aid 1 of the present embodiment illustrated in FIG. 1 is used for aiding the insertion of a surgical tool into the body.

The surgical tool insertion aid 1 is a flexible tubular body which is made from a flexible plastic such as polypropylene or vinyl chloride or from rubber or the like. A plurality of inner tubes 2a, 2b and 2c (may be abbreviated as "2") can be inserted inside the surgical tool insertion aid 1. The surgical tool insertion aid 1 comprises a plurality of guide members 3 that are extended in the axial direction from a distal end side to a proximal end side on an inner peripheral surface thereof.

Figure 2A:
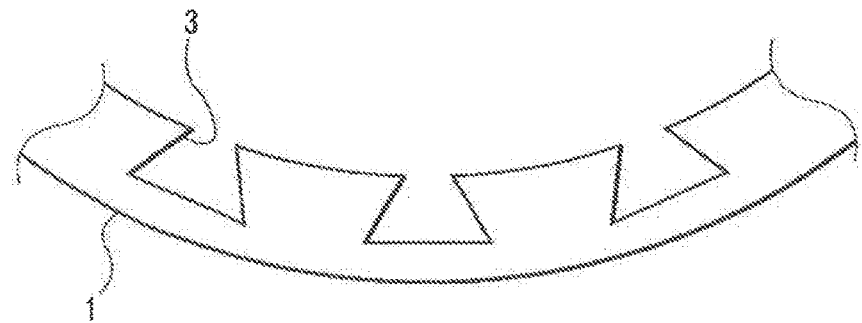
Figure 2B:
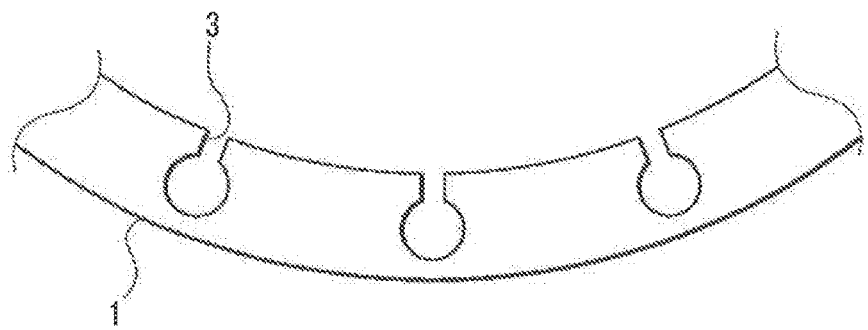
Figure 2C:
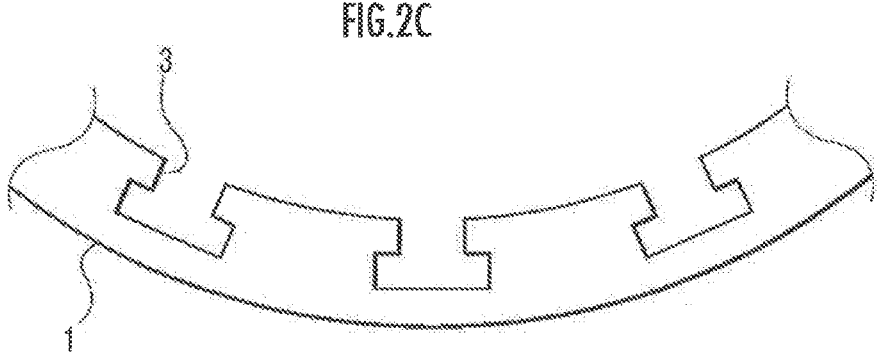

The guide members 3 are dovetail grooves that are formed in an inner wall surface of the surgical tool insertion aid 1. Although in the present embodiment, as illustrated in FIG. 2A, the dovetail grooves have an approximately trapezoidal cross-sectional shape that expands more to the inner side relative to the opening, the dovetail grooves may have a cross-sectional shape in which the opening is rectangular and the inner side is an approximately circular cross-sectional shape as illustrated in FIG. 2B, or may have a cross-sectional shape in which the opening and the inner side each have a rectangular cross-sectional shape as illustrated in FIG. 2C.

Further, between adjacent guide members 3 and 3 in the peripheral wall surface of the surgical tool insertion aid 1, a first wire member 6 is embedded in the axial direction from the distal end side to the proximal end side. The first wire member 6 extends further rearward than the proximal end portion of the surgical tool insertion aid 1, and by grasping and operating a first wire member operating portion 15a (see FIG. 6) at which the proximal end portion of the first wire member 6 is provided, the surgical tool insertion aid 1 can be caused to bend in a circumferential direction to point the distal end portion thereof in a desired direction. By temporarily fixing an operation of the first wire member operating portion 15a by means of, for example, a ratchet mechanism (corresponds to "first wire fixing device" of the present invention), the shape of the first wire member 6 can be temporarily fixed so that the distal end portion of the surgical tool insertion aid 1 can be maintained in a state in which the distal end portion points in a predetermined direction.

The inner tube 2 is a flexible tubular body made of the aforementioned flexible plastic. A surgical tool such as an endoscope or a forceps can be inserted through the inside of the inner tube 2. The inner tube 2 may have one channel for inserting the surgical tool or may have two or more channels for inserting the surgical tools. The outer peripheral surface of the inner tube 2 is subjected to a hydrophilic treatment.

In the present embodiment, the inner tube 2 includes, in the order of a larger inner diameter and outer diameter, a first inner tube 2a having a first inner diameter and a first outer diameter, a second inner tube 2b having a second inner diameter and a second outer diameter, and a third inner tube 2c having a third inner diameter and a third outer diameter. The inner tubes 2a, 2b and 2c are color-coded so as to be distinguishable from each other.

The inner tube 2 comprises, from a distal end to a proximal end of the outer peripheral surface thereof, an engaging member 4 that engages with the guide member 3 to be made slidable, and a scale (not illustrated in the drawings) for ascertaining an insertion depth, and also comprises a bendable bending portion 19 (see FIG. 6) at the distal end portion thereof. Each inner tube 2 can be inserted into and withdrawn from the inside of the surgical tool insertion aid 1 in accordance with a procedure.

The engaging member 4 has a cross-sectional shape the width of which expands from the inner diameter side to the outer diameter side of the inner tube 2. Although in the present embodiment the engaging member 4 has a cross-sectional shape that is approximately trapezoidal, the engaging member 4 can be formed in any shape as long as the engaging member 4 can engage with the guide member 3.

Figure 3A:
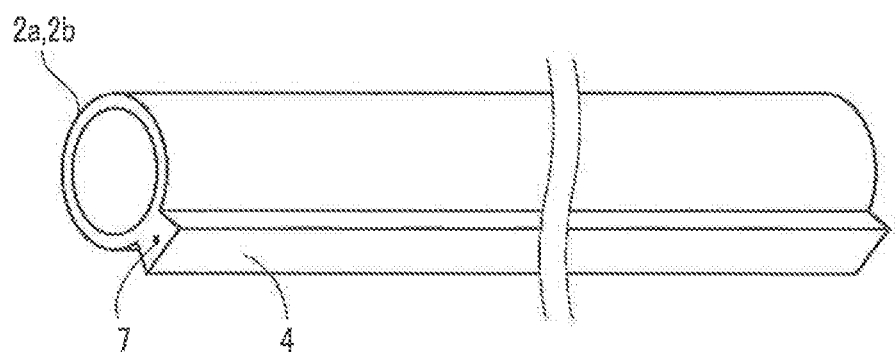
Figure 3B:
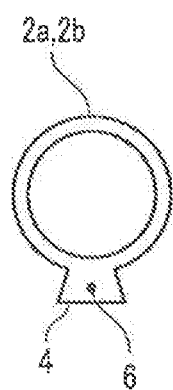
Figure 3C:
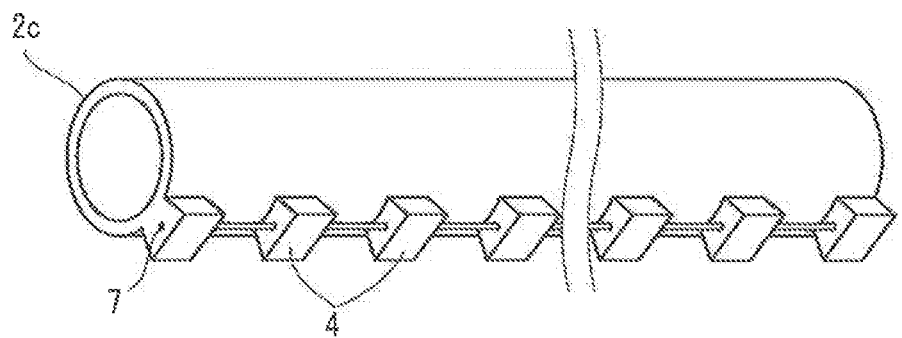

The engaging member 4 can be provided from the distal end to the proximal end of the inner tube 2, or alternatively a configuration can be adopted in which engaging members 4 are provided at part of an area from the distal end to the proximal end of the outer peripheral surface of the inner tube 2, with at least one of the engaging members 4 being provided at the distal end. In the present embodiment, as illustrated in FIGS. 3A and 3B, on the inner tubes 2a and 2b, a long engaging member 4 is provided continuously from the distal end to the proximal end of the inner tubes 2, while on the inner tube 2c, as illustrated in FIG. 3C, a plurality of short engaging members 4 are intermittently provided from the distal end to the proximal end thereof. Further, although not illustrated in the drawings, a configuration may also be adopted in which the engaging member is provided only at a distal end of the outer periphery of the inner tube.

Further, in the engaging member 4 of the inner tube 2, a second wire member 7 is embedded from the distal end side to the proximal end side in the axial direction. The second wire member 7 extends further rearward than the proximal end portion of the inner tube 2, and a second wire member operating portion 15b (see FIG. 6) at which the proximal end portion of the second wire member 7 is provided can be grasped and operated. It is only necessary that the second wire member 7 is a member which is fixed to the inner tube 2, and instead of being embedded in the engaging member 4, the second wire member 7 may be embedded in a peripheral wall of the inner tube 2 or may be adhered to the outer peripheral surface of the inner tube 2.

When the distal end portion of the tube 2 of an inner endoscope 11 or a surgical tool 13 protrudes from the distal end of the surgical tool insertion aid 1, the second wire member 7 can be caused to bend in a circumferential direction by the bending portion 19 of the inner tube 2 so as to point the distal end portion thereof in a desired direction. Further, at a time when the distal end portion of the inner tube 2 is not protruding from the distal end of the surgical tool insertion aid 1, and the inner tube 2 is housed within the surgical tool insertion aid 1, the second wire member 7 can cause the surgical tool insertion aid 1 to bend in a manner that follows bending of the inner tube 2.

By temporarily fixing an operation of the second wire member operating portion 15b by means of for example, a ratchet mechanism (corresponds to "second wire fixing device" of the present invention), the shape of the second wire member 7 can be temporarily fixed so that the distal end portion of the inner tube 2 or the surgical tool insertion aid 1 can be maintained in a state in which the distal end portion points in a predetermined direction.

The bending portion 19 of the inner tube 2 may be a component that is capable of bending in any direction with respect to the circumferential direction, or may be a component that is capable of bending in only specific directions. The bending portion 19 that is capable of bending in only specific directions can be realized, for example, by adopting the configurations illustrated in FIGS. 4 and 5.

Figure 4A:
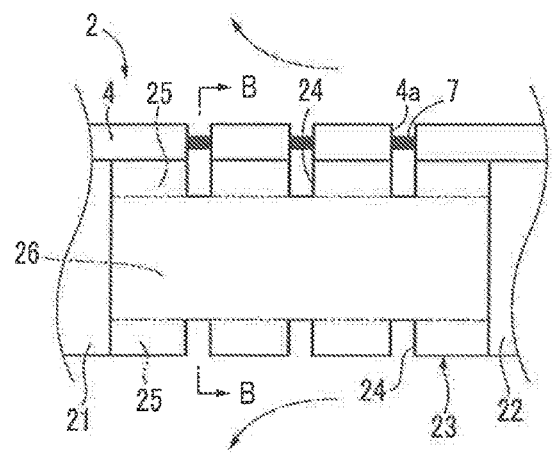
Figure 4B:
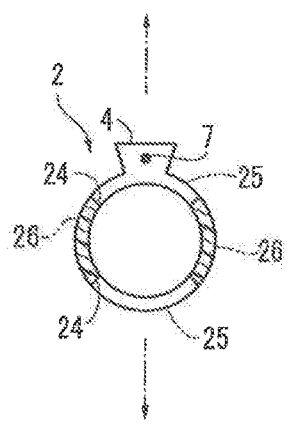

The inner tube 2 illustrated in FIGS. 4A and 4B comprises a distal end side tube 21 and a proximal end side tube 22 which are made of a flexible resin such as polypropylene or vinyl chloride, and a middle tube 23 which connects the tubes 21 and 22 and which is made of a material (for example, stainless steel) that has less flexibility than the tubes 21 and 22. In a peripheral wall portion of the middle tube 23, three hole portions 24 having a substantially "I" shape are provided so as to face each other in a region on an upper side and a region on a lower side in FIG. 4B, respectively. The hole portions 24 penetrate through the outer peripheral surface of the middle tube 23 along the circumferential direction, and have a width equivalent to around one-quarter of the peripheral length of the middle tube 23. Providing the three hole portions 24 in a line in the length direction of the middle tube 23 means that portions with a hole 25 are formed in the length direction in the outer peripheral surface of the middle tube 23, and portions without a hole 26 in which the hole portions 24 are not formed are provided between one of the portions with a hole 25 and another of the portions with a hole 25. In addition, each engaging member 4 includes a hole portion 4a that communicates with the respective hole portions 24, and the second wire member 7 is exposed at the hole portions 4a.

By adopting the above-described configuration, although the inner tube 2 illustrated in FIGS. 4A and 4B can, at the bending portion 19, bend in the directions of the portions with a hole 25 and the distal end portion thereof can point in specific directions (in this case, the upper and lower directions that are indicated by arrows in FIG. 4B) by means of an operation of the second wire member operating portion 15b, the inner tube 2 cannot bend in the directions of the portions without a hole 26, and hence the distal end portion thereof cannot point in the left or right direction. According to this configuration, the distal end of the inner tube 2 can only point in directions that the surgeon desires.

Figure 4C:
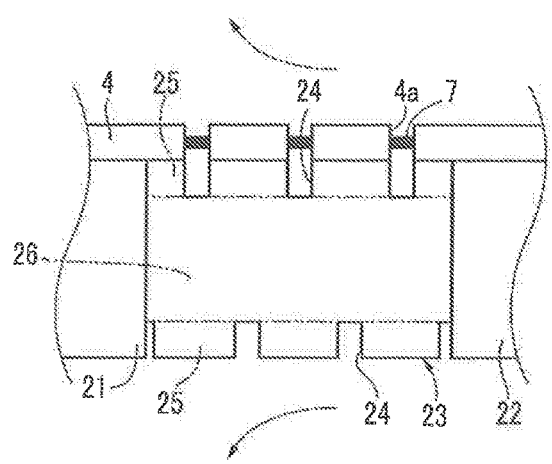

As illustrated in FIG. 4C, the configuration of the bending portion 19 that only bends in specific directions may be a configuration which comprises, in the outer peripheral surface of the middle tube 23, three hole portions 24 in a region on the upper side in FIG. 4C and four hole portions 24 in a region on the lower side in FIG. 4C, in which the hole portions 24 are arranged in lines so as to be in a staggered arrangement.

Figure 5A:
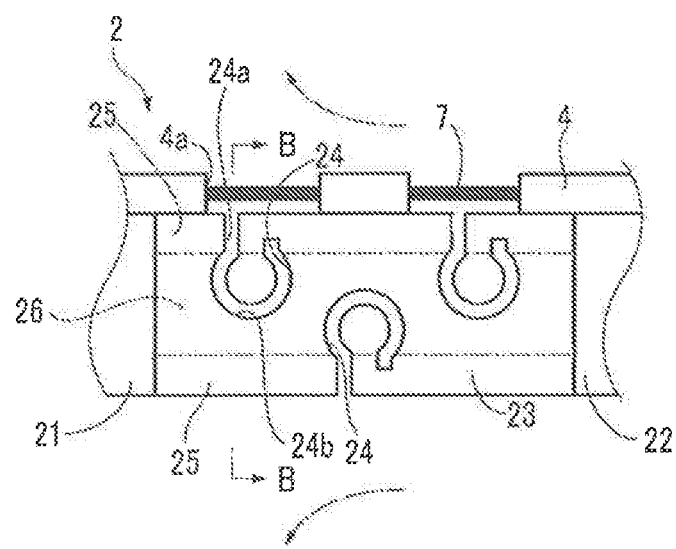
Figure 5B:
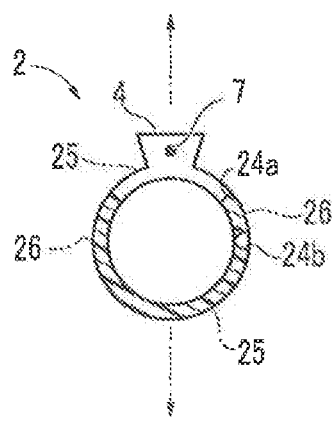

Further, as illustrated in FIGS. 5A and B, the bending portion 19 may be a portion that comprises two hole portions 24 having a shape in which a substantially "?" shape is connected to a leg portion 24a in a region on an upper side and a region on a lower side in FIG. 5B which are regions in the outer peripheral surface of the middle tube 23. In this case, the portions with a hole 25a are formed by the leg portion 24a of each hole portion 24 being formed along the circumferential direction of the middle tube 23 and a plurality of the leg portions 24a being arranged in a line in the length direction, and the portions without a hole 26 are formed between one of the portions with a hole 25 and the other portion with a hole 25. Although an arc-shaped portion 24b of the hole portion 24 is located in the portions without a hole 26, the leg portion 24a is not located therein. Consequently, the inner tube 2 is not bent in the directions of the portions without a hole 26 in the bending portion 19 and is bent only in the directions of the portions with a hole 25, and thus the distal end portion of the inner tube 2 can point in specific directions (in this case, the upper and lower directions indicated by arrows in FIG. 4B).

Furthermore, although not illustrated in the drawings, in the bending portion 19 that is capable of bending in only specific directions, a tube which is made of a material that is less flexible than the inner tube 2 may be mounted on an outer peripheral side of an area that is separated by a predetermined distance from the distal end of the inner tube 2, with the tube comprising portions with a hole and portions without a hole as shown in FIGS. 4 and 5. That is, in a peripheral wall portion thereof, the tube may comprise, in a length direction, portions with a hole in which hole portions which are formed along the circumferential direction are arranged in a line in the length direction, and portions without a hole in which the hole portion is not formed which are respectively provided between one portion with a hole and another portion with a hole.

Figure 6:
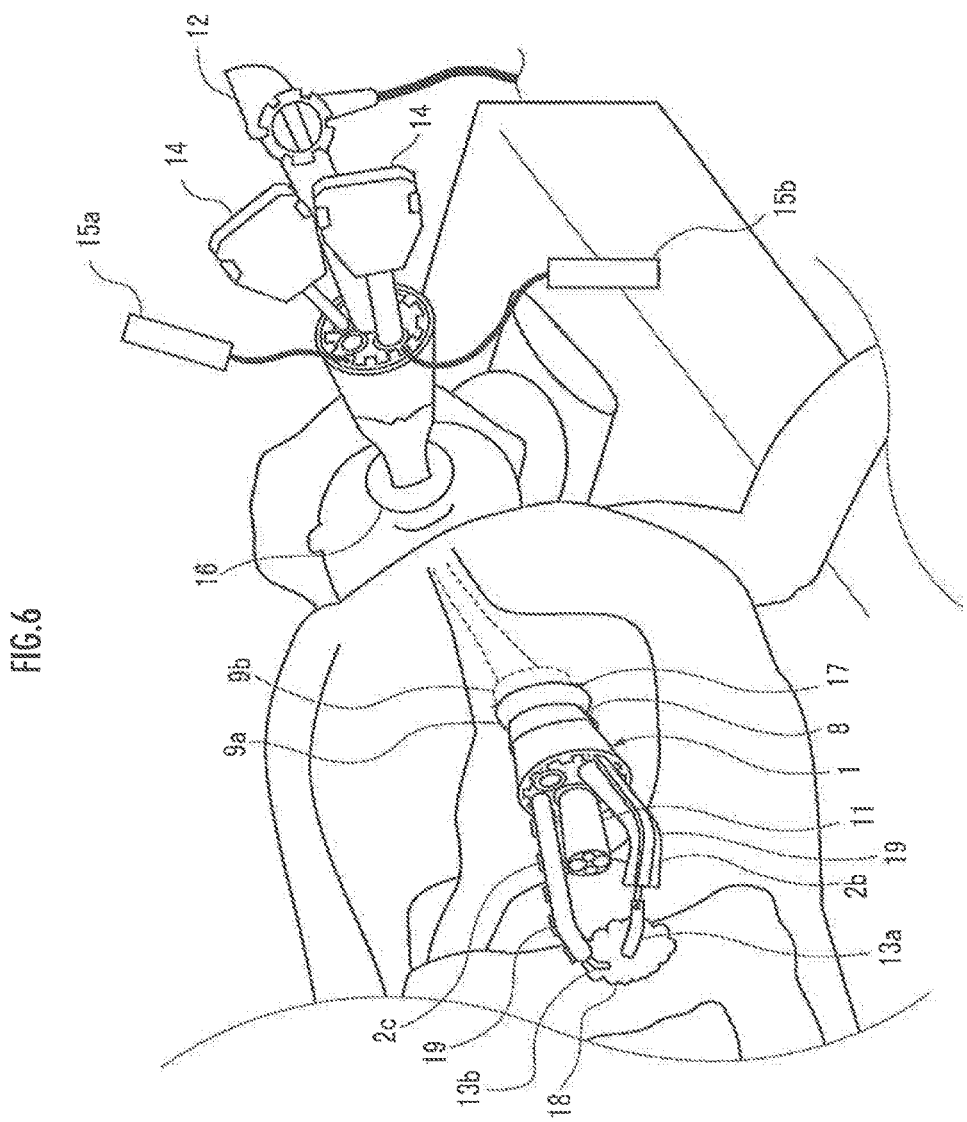
FIG. 6 is an explanatory drawing illustrating a first usage state of the surgical tool insertion aid.

In addition, as illustrated in FIG. 6, on the outer peripheral surface of the surgical tool insertion aid 1, an outer tube 8 is mounted that can advance and retract with respect to the surgical tool insertion aid 1 and which is rotatable about the surgical tool insertion aid 1 as an axis. The outer tube 8 is a flexible tubular body which is made from the aforementioned flexible plastic, and whose outer peripheral surface is subjected to a hydrophilic treatment. Furthermore, two balloon members 9a and 9b which are contractible and expandable so as to protrude in an outer periphery direction are provided partway along the outer peripheral surface of the outer tube 8. An air-feeding tube which is connected to an air-feeding apparatus is connected to the balloon members 9a and 9b.

Further, an unshown degassing prevention cap for a surgical tool insertion aid (corresponds to first degassing prevention cap of the present invention) is mounted at the proximal end portion of the surgical tool insertion aid 1, and an unshown degassing prevention cap for an inner tube (corresponds to second degassing prevention cap of the present invention) is mounted at the proximal end portion of each inner tube 2 (the respective caps are described later). According to the degassing prevention cap for a surgical tool insertion aid, leaking of air that is inside the body cavity from a place at which the inner tube 2 of the surgical tool insertion aid 1 is not inserted or from the outer peripheral portion of the inner tube 2 that is inserted can be prevented. According to the degassing prevention cap for an inner tube, leaking of air that is inside the body cavity from the inner tube 2 into which the surgical tool 13 is not inserted can be prevented.

Further, an endoscope operating portion 12 for operating the endoscope 11 as a surgical tool, a surgical tool operating portion 14 for operating surgical tools 13a and 13b (may be abbreviated as "13"), and the first wire member operating portion 15a and the second wire member operating portion 15b for operating the first wire member 6 and the second wire member 7 are connected to the proximal end portion of each inner tube 2.

Next, a method of using the surgical tool insertion aid 1 will be described referring to FIG. 1 to FIG. 6. In the present embodiment, a case of performing natural orifice translumenal endoscopic surgery (NOTES) is described.

First, in a state in which the inner tubes 2a, 2b and 2c are inserted inside the surgical tool insertion aid 1, as illustrated in FIG. 6, a mouthpiece 16 is placed in the mouth of a patient, the surgical tool insertion aid 1 is inserted from the mouthpiece 16, and the distal end portion of the surgical tool insertion aid 1 is caused to arrive at the stomach via the throat and esophagus.

Next, the endoscope 11 is inserted into the first inner tube 2a, and a forceps 13a and a scalpel 13b are inserted into the second inner tube 2b and the third inner tube 2c. At this time, the state is one in which the endoscope 11, forceps 13a and scalpel 13b do not protrude from the distal end of the surgical tool insertion aid 1 and remain inside the surgical tool insertion aid 1.

Next, by operation of the endoscope operating portion 12 and the surgical tool operating portion 14, the endoscope 11, forceps 13a and scalpel 13b are caused to protrude from the distal end of the surgical tool insertion aid 1, an opening 17 is formed as a route of entry in the gastric wall by the scalpel 13b, and the surgical tool insertion aid 1 is caused to enter from the opening 17 to the outside of the gastric wall.

Subsequently, by positioning the gastric wall between the two balloon members 9a and 9b and inflating the balloon members 9a and 9b, the gastric wall is sandwiched and fixed by the balloon members 9a and 9b, and the open state of the opening 17 is maintained.

In addition, by causing the surgical tool insertion aid 1 to protrude from the outer tube 8 and advancing the surgical tool insertion aid 1, and as necessary, operating the first wire member 6 and the second wire member 7 by means of the first wire member operating portion 15a and the second wire member operating portion 15b to bend the surgical tool insertion aid 1 in the circumferential direction and point the distal end portion thereof in a desired direction, the distal end portion of the surgical tool insertion aid 1 is caused to face a site to be treated 18 in the abdominal viscera.

Next, the distal end portions of the inner tube 2b and the inner tube 2c are pointed in the desired direction and caused to face the site to be treated 18 by operating the second wire member 7 by means of the second wire member operating portion 15b to bend the second inner tube 2b and the third inner tube 2c at the bending portion 19. Subsequently, treatment is performed by causing the forceps 13a and the scalpel 13b to protrude from the distal end of the inner tube 2.

At this time, in a case where the position of the surgical tool 13 is located away from the site to be treated 18, by causing the surgical tool insertion aid 1 to rotate relative to the outer tube 8, the inner tube 2 through which the required surgical tool 13 is inserted can be aligned with the desired position and the surgical tool 13 can be brought close to the site to be treated 18.

In this connection, in some cases it is desired to exchange, for example, the forceps 13a for another surgical tool during surgery. In a case where the outer diameter of the other surgical tool is smaller than the outer diameter of the forceps 13a, the forceps 13a can be exchanged for the other surgical tool by taking the forceps 13a out from the second inner tube 2b and inserting the other surgical tool into the second inner tube 2b. However, if the inner diameter of the other surgical tool is larger than the inner diameter of the second inner tube 2b, the other surgical tool cannot be inserted into the second inner tube 2b.

Therefore, in the surgical tool insertion aid 1 of the present embodiment, the forceps 13a is withdrawn together with the second inner tube 2b, and the first inner tube 2a having a larger inner diameter than the inner diameter of the second inner tube 2b is inserted. At this time, if there is no space into which the first inner tube 2a can be inserted inside the surgical tool insertion aid 1, the first inner tube 2a is inserted after securing the space by withdrawing other inner tubes 2b and 2c that are mounted in the surgical tool insertion aid 1. Thereafter, the other surgical tool is inserted into the first inner tube 2a to thereby complete the operation to exchange the forceps 13a for the other surgical tool.

According to the surgical tool insertion aid 1 of the present embodiment, by causing the engaging member 4 of the inner tube 2 to engage with and slide along the guide member 3 that is extended in the axial direction from the distal end side to the proximal end side, the first inner tube 2a can be smoothly inserted and withdrawn in a state in which the position thereof relative to other inner tubes 2 that are mounted inside the surgical tool insertion aid 1 is maintained, and a desired surgical tool can be used.

As described above, according to the surgical tool insertion aid 1 of the present embodiment, the diameters and number of the inner tubes 2 can be freely changed, and the surgical tool 13 can be individually exchanged during surgery and a desired surgical tool 13 can be used.

Further, in the surgical tool insertion aid 1 of the present embodiment, since the engaging members 4 of the inner tubes 2a and 2b are provided from the distal end to the proximal end, the inner tubes 2a and 2b can be smoothly inserted into and withdrawn from the interior of the surgical tool insertion aid 1. Further, since the engaging members 4 of the inner tube 2c are intermittently provided from the distal end to the proximal end, the inner tube 2c can be smoothly inserted and withdrawn even in a state in which the entire surgical tool insertion aid 1 is curved.

Further, according to the surgical tool insertion aid 1 of the present embodiment, since the outer tube 8 comprising the balloon members 9a and 9b is capable of advancing and retracting relative to the surgical tool insertion aid 1 and is rotatably mounted thereto, after sandwiching the gastric wall with the balloon members 9a and 9b and fixing the outer tube 8, the distal end portion of the surgical tool insertion aid 1 can be brought closer to the site to be treated 18 by advancing or rotating only the surgical tool insertion aid 1. Further, since the gastric wall is sandwiched by the balloon members 9a and 9b, air or body fluid or the like can be prevented from leaking out from the opening 17.

Furthermore, although in the present embodiment a method is described in which the outer tube 8 is mounted to the surgical tool insertion aid 1 and used, it is also possible to use the surgical tool insertion aid 1 without mounting the outer tube 8.

Although in the present embodiment a method is described in which the surgical tool insertion aid 1 is used when performing NOTES, the surgical tool insertion aid 1 can also be used in the case of opening a route of entry in the skin and mucous membrane on the body surface and inserting the surgical tool insertion aid 1 into the body from the opening.

Figure 7:
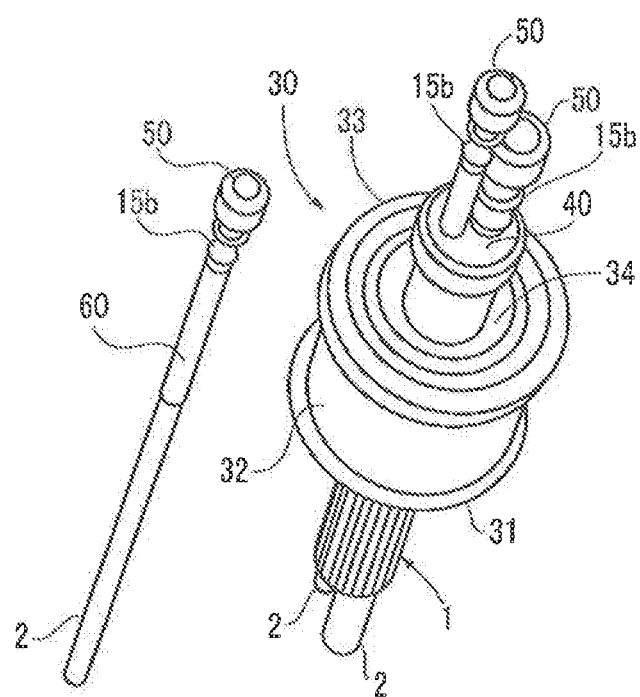
FIG. 7 is an explanatory drawing illustrating a second usage state of the surgical tool insertion aid.

Furthermore, although in the present embodiment an open state of the opening 17 is maintained (see FIG. 6) by sandwiching and fixing the luminal wall between the balloon members 9a and 9b, a retractor 30 may be used instead of the balloon members 9a and 9b, as illustrated in FIG. 7. For example, a retractor disclosed in Japanese Patent Laid-Open No. 2014-39703 can be used as the retractor 30.

The retractor 30 comprises a ring-shaped inside fixing member 31 to be disposed inside a body cavity, a ring-shaped outside fixing member (not illustrated in the drawing) to be disposed outside a body cavity, and a tubular expansion member 32 that connects the inside fixing member 31 and the outside fixing member and expands an opening (not illustrated in the drawing) and maintains an open state thereof. In the retractor 30, a valve cap for a retractor 33 is mounted to the outside fixing member. The valve cap for a retractor 33 comprises a sheet member 34 which blocks an opening of the outside fixing member and is made from a flexible material such as polyurethane. The surgical tool insertion aid 1 is introduced through a slit portion (not illustrated in the drawing) that penetrates through the sheet member 34 of the valve cap for a retractor 33 in the thickness direction.

Next, a degassing prevention cap for a surgical tool insertion aid 40 that is mounted to the surgical tool insertion aid 1, a degassing prevention cap for an inner tube 50 that is mounted to the proximal end of the inner tube 2, and a level-difference eliminating tube 60 that is mounted to the proximal end of the inner tube 2 are described referring to FIG. 7 to FIG. 10.

Figure 8A:
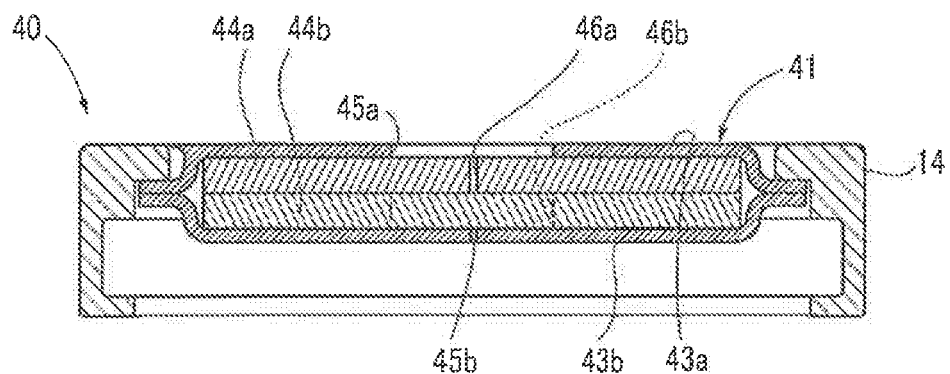
Figure 8B:
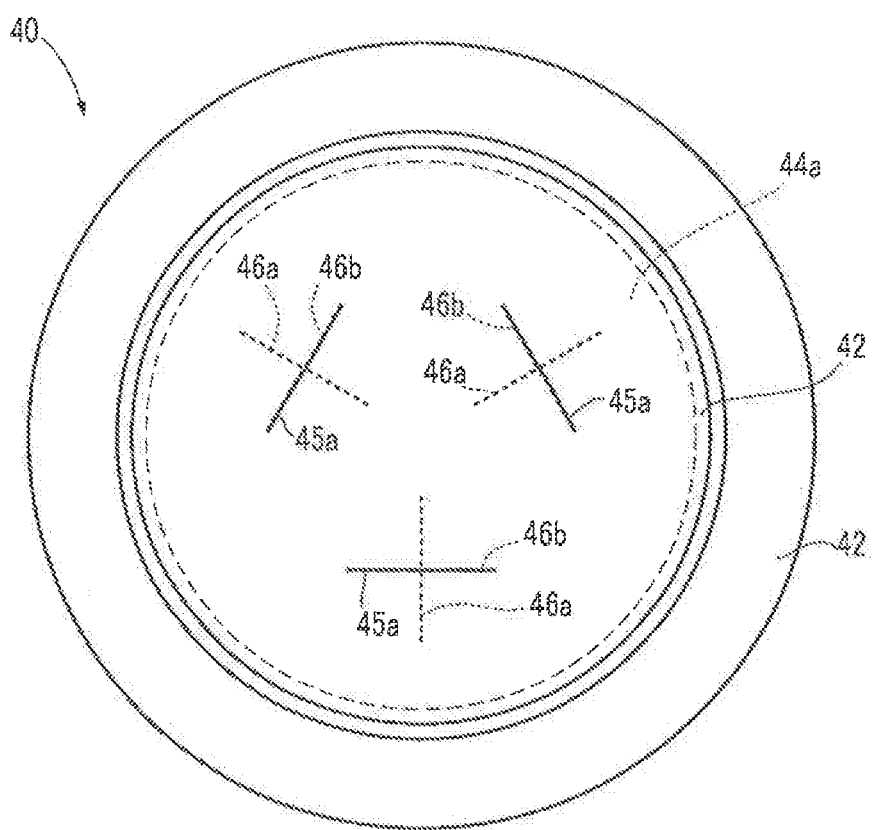

The degassing prevention cap for a surgical tool insertion aid 40 illustrated in FIG. 8 comprises a round canopy member 41, and a mounting ring 42 for airtightly mounting the canopy member 41 to the surgical tool insertion aid 1. The canopy member 41 includes two surface-layer-side sheet members 43a and 43b that are positioned on the front surface and rear surface of the canopy member, and two inner-layer-side sheet members 44a and 44b that are layered between the surface-layer-side sheet members 43a and 43b. The surface-layer-side sheet members 43a and 43b are made of a flexible resin such as silicone rubber, polyurethane or polyethylene. The inner-layer-side sheet members 44a and 44b are made of a flexible resin such as polyurethane, polyvinyl chloride or polyethylene that has an elastic property and also has a slipping property with respect to the surface-layer-side sheet members 43a and 43b.

The surface-layer-side sheet member 43a that is on the front surface side comprises a first surface-layer-side slit 45a that penetrates in the thickness direction thereof at a position at which the inner tube 2 is insertable into the surgical tool insertion aid 1. Further, the inner-layer-side sheet member 44a on the rear surface side, the inner-layer-side sheet member 44b on the rear surface side and the surface-layer-side sheet member 43a on the rear surface side comprise, at positions that correspond to the first surface-layer-side slit 45a, a first inner-layer-side slit 46a, a second inner-layer-side slit 46b and a second surface-layer-side slit 45b, respectively. The first surface-layer-side slit 45a the first inner-layer-side slit 46a, the second inner-layer-side slit 46b and the second surface-layer-side slit 45b are formed so as to intersect with each other, and therefore the inner tube 2 can be introduced in an airtight manner.

Figure 9A:
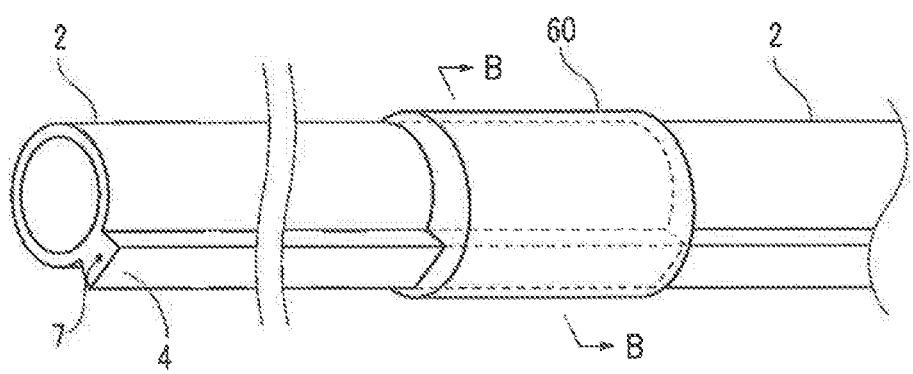
Figure 9B:
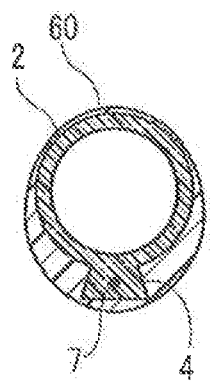

In addition, as illustrated in FIG. 8 and FIG. 9, a level-difference eliminating tube 60 that fills a level difference between the outer peripheral surface of the inner tube 2 and the outer peripheral surface of the engaging member 4 is mounted at a portion at the proximal end of the inner tube 2 which is a portion that is introduced into the first degassing prevention cap 40. As illustrated in FIG. 9B, the outer peripheral surface of the level-difference eliminating tube 60 has an approximately elliptic shape, and the inner peripheral surface thereof has a shape which fills a level difference that arises as a result of the engaging member 4 protruding from the outer peripheral surface of the inner tube 2.

Figure 10A:
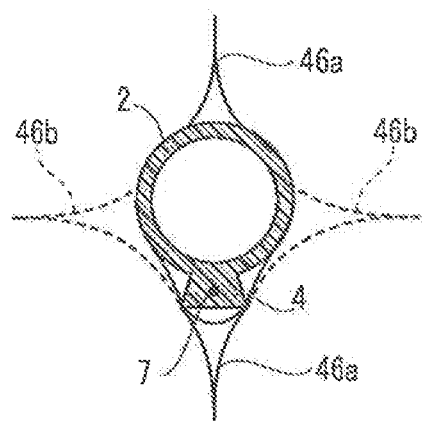

If the inner tube 2 to which the level-difference eliminating tube 60 is not mounted is introduced into the degassing prevention cap for a surgical tool insertion aid 40, as illustrated in FIG. 10A, a large gap arises between the first and second inner-layer-side slits 46a and 46b and the outer peripheral surface of the inner tube 2 or outer peripheral surface of the engaging member 4 due to the level difference that arises as a result of the engaging member 4 protruding from the outer peripheral surface of the inner tube 2.

Figure 10B:
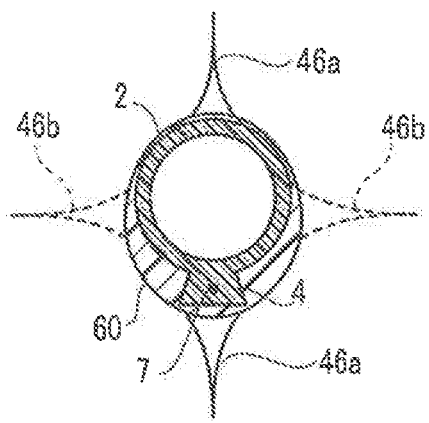

On the other hand, if the inner tube 2 to which the level-difference eliminating tube 60 is mounted is introduced into the degassing prevention cap for a surgical tool insertion aid 40, because the aforementioned level difference is filled by the level-difference eliminating tube 60, as illustrated in FIG. 10B, a gap that arises between the first and second inner-layer-side slits 46a and 46b and the outer peripheral surface of the level-difference eliminating tube 60 can be reduced, and the airtightness inside the body cavity can be further maintained.

Note that, in the inner tube 2 illustrated in FIG. 7, the second wire member operating portion 15b is provided on the proximal end side of the level-difference eliminating tube 60, and the degassing prevention cap for an inner tube 50 is also mounted on the proximal end side thereof.

The degassing prevention cap for an inner tube 50 comprises an opening and closing valve (not illustrated in the drawings) that is capable of oscillating from the outward side to the inward side. The opening and closing valve opens to the inward side accompanying introduction of the endoscope 11 or the surgical tool 13, and the valve closes accompanying withdrawal of the endoscope 11 or the surgical tool 13 to thereby block the inner tube 2. According to the degassing prevention cap for an inner tube 50, air inside the body cavity can be prevented from leaking out from the inner tube 2 in which the endoscope 11 or the surgical tool 13 is not inserted.

REFERENCE SIGNS LIST

1 . . . surgical tool insertion aid; 2, 2a, 2b, 2c . . . inner tube; 3 . . . guide member; 4 . . . engaging member; 6 . . . first wire member; 7 . . . second wire member; 8 . . . outer tube; 9a, 9b . . . balloon member; 11, 13 . . . surgical tool; 19 . . . bending portion; 43a, 43, 44a, 44b . . . first sheet member, second sheet member; 45a, 45b, 46a, 46b . . . first slit portion, second slit portion; 40 . . . first degassing prevention cap; 50 . . . second degassing prevention cap; 60 . . . level-difference eliminating portion.

The invention claimed is:

1. A surgical tool insertion aid having a tubular body and which aids insertion of a surgical tool into a body, comprising:
    a plurality of inner tubes into which the surgical tool is insertable and which are insertable into the tubular body of the surgical tool insertion aid, and which include at least one inner tube and another inner tube having a smaller diameter than the at least one inner tube; and
    a plurality of guide members which are extended in an axial direction from a distal end side to a proximal end side in an inner peripheral surface of the tubular body of the surgical tool insertion aid, and in which cross-sections perpendicular to the axial direction are of identical shapes;
    wherein each of the plurality of inner tubes comprises, on an outer peripheral surface, an engaging member which slidably engages with a respective guide member of the plurality of guide members, and
    the plurality of inner tubes are held in the tubular body of the surgical tool insertion aid by the engaging member of each of the plurality of inner tubes engaging the respective guide member, and the engaging member of each of the plurality of inner tubes is independently slidable with respect to the respective guide member of the plurality of guide members by a bending of the surgical tool insertion aid.

2. The surgical tool insertion aid according to claim 1, wherein:
    the engaging member of each of the plurality of inner tubes is provided from a distal end to a proximal end of the outer peripheral surface of the respective inner tube.

3. The surgical tool insertion aid according to claim 1, wherein:
    the engaging member of each of the plurality of inner tubes is provided at part of an area from a distal end to a proximal end of the outer peripheral surface of the respective inner tube, and the engaging member of at least one of the plurality of inner tubes is provided at the distal end.

4. The surgical tool insertion aid according to claim 1, wherein:
    the outer peripheral surface of each of the plurality of inner tubes is subjected to a hydrophilic treatment.

5. The surgical tool insertion aid according to claim 1, comprising:
    a first wire member which is embedded within a peripheral wall of the tubular body of the surgical tool insertion aid in the axial direction from the distal end side to the proximal end side thereof, and whose proximal end portion can be grasped and operated so as to cause the surgical tool insertion aid to bend in an arbitrary direction.

6. The surgical tool insertion aid according to claim 5, comprising:
    a first wire fixing device which temporarily fixes an operation of the first wire member.

7. The surgical tool insertion aid according to claim 1, comprising:
    a plurality of second wire members, each of which is fixed in a respective one of the plurality of inner tubes and has a proximal end portion that can be grasped and operated so as to cause the respective inner tube to bend in an arbitrary direction.

8. The surgical tool insertion aid according to claim 7, comprising:
    a second wire fixing device which temporarily fixes an operation of the second wire member.

9. The surgical tool insertion aid according to claim 7, wherein:
    each of the plurality of inner tubes comprises, on a distal end side, a bending portion that can be bent by an operation of the respective second wire member.

10. The surgical tool insertion aid according to claim 9, wherein:
    in each of the plurality of inner tubes, bending directions of the bending portion are limited.

11. The surgical tool insertion aid according to claim 1, comprising:
    a first degassing prevention cap which is mounted at a proximal end portion of the tubular body of the surgical tool insertion aid and which is capable of introducing the plurality of inner tubes.

12. The surgical tool insertion aid according to claim 11, wherein:
    the first degassing prevention cap comprises a flexible sheet member which blocks the proximal end portion of the tubular body of the surgical tool insertion aid, and
    the sheet member comprises a slit portion which penetrates in a thickness direction and which is provided for introducing the plurality of inner tubes.

13. The surgical tool insertion aid according to claim 11, wherein:
    the engaging member of each of the plurality of inner tubes is provided from a distal end to a proximal end of the outer peripheral surface of the respective inner tube; and
    each of the plurality of inner tubes comprises, within a first predetermined distance from the proximal end thereof, a level-difference eliminating portion which fills a level difference between the outer peripheral surface of the inner tube and an outer peripheral surface of the respective engaging member.

14. The surgical tool insertion aid according to claim 1, comprising:
    a second degassing prevention cap which is mounted at a proximal end portion of each of the plurality of inner tubes and which is capable of introducing the surgical tool.

15. The surgical tool insertion aid according to claim 14, wherein:
    the second degassing prevention cap is an opening and closing valve which is capable of introducing the surgical tool.

16. The surgical tool insertion aid according to claim 1, comprising:
    on an outer peripheral side of the tubular body of the surgical tool insertion aid, an outer tube which is mounted in an advanceable and retractable manner with respect to the tubular body of the surgical tool insertion aid, or is rotatably mounted with respect to the tubular body of the surgical tool insertion aid as an axis.

17. The surgical tool insertion aid according to claim 16, comprising:
- two balloon members which are provided on the outer peripheral surface of the outer tube and which are contractible and expandable so as to protrude in an outer periphery direction;
- wherein a predetermined gap is provided between the two balloon members.

\* \* \* \* \*